United States Patent
Aho et al.

(10) Patent No.: US 10,842,920 B2
(45) Date of Patent: Nov. 24, 2020

(54) CO2-SENSING CHEST TUBE AND NEEDLE THORACOSTOMY DEVICES

(71) Applicant: Mayo Foundation for Medical Education and Research, Rochester, MN (US)

(72) Inventors: Johnathon M. Aho, Rochester, MN (US); Raaj K. Ruparel, Rochester, MN (US); Phillip G. Rowse, Rochester, MN (US); Cornelius A. Thiels, Rochester, MN (US); Twinkle Kumar Pandian, Rochester, MN (US); Nimesh D. Naik, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 821 days.

(21) Appl. No.: 15/534,126

(22) PCT Filed: Dec. 9, 2015

(86) PCT No.: PCT/US2015/064776
§ 371 (c)(1),
(2) Date: Jun. 8, 2017

(87) PCT Pub. No.: WO2016/094548
PCT Pub. Date: Jun. 16, 2016

(65) Prior Publication Data
US 2017/0368241 A1    Dec. 28, 2017

Related U.S. Application Data

(60) Provisional application No. 62/089,909, filed on Dec. 10, 2014.

(51) Int. Cl.
*A61M 1/00*    (2006.01)

(52) U.S. Cl.
CPC ... *A61M 1/0088* (2013.01); *A61M 2205/6081* (2013.01); *A61M 2210/101* (2013.01); *A61M 2230/432* (2013.01)

(58) Field of Classification Search
CPC .......... A61M 1/0088; A61M 2230/432; A61M 2210/101; A61M 2016/0413; A61B 5/0836
See application file for complete search history.

(56) References Cited

U.S. PATENT DOCUMENTS 5,005,572 A    4/1991   Raemer et al.
5,124,129 A *  6/1992   Riccitelli .......... A61M 16/0488
                                           128/207.14

(Continued)

FOREIGN PATENT DOCUMENTS

WO    WO 2013/123338    8/2013

OTHER PUBLICATIONS

Bailey, "Complications of tube thoracostomy in trauma," J Accid Emerg Med., 17(2):111-114, Mar. 2000.

(Continued)

*Primary Examiner* — Ariana Zimbouski
(74) *Attorney, Agent, or Firm* — Fish & Richardson P.C.

(57) ABSTRACT

This document provides systems and methods that can improve the efficacy of tube and needle thoracostomy. For example, this document provides devices and methods for confirming the proper placement of a chest tube or needle within the pleural space to relieve a pneumothorax or tension pneumothoax.

11 Claims, 5 Drawing Sheets

(56) References Cited

U.S. PATENT DOCUMENTS

| | | |
|---|---|---|
| 5,738,656 A | 4/1998 | Wagner |
| 5,743,259 A | 4/1998 | Kruse et al. |
| 6,029,076 A | 2/2000 | Fiddian-Greene et al. |
| 6,770,070 B1 | 8/2004 | Balbierz |
| 8,083,684 B2 | 12/2011 | Palatnik |
| 8,246,752 B2 | 8/2012 | Boyle, Jr. |
| 8,420,405 B2 | 4/2013 | Ostrowski et al. |
| 8,454,526 B2 | 6/2013 | Baker, Jr. et al. |
| 2003/0018309 A1 | 1/2003 | Breznick |
| 2003/0121812 A1 | 7/2003 | Sprieck et al. |
| 2004/0006311 A1 | 1/2004 | Shchervinsky |
| 2004/0065329 A1* | 4/2004 | Geist ............ A61M 16/085 128/207.14 |
| 2004/0148140 A1 | 7/2004 | Tarassenko et al. |
| 2005/0240093 A1 | 10/2005 | DeArmond |
| 2006/0155206 A1 | 7/2006 | Lynn |
| 2007/0078444 A1 | 4/2007 | Larsson |
| 2008/0077035 A1 | 3/2008 | Baker et al. |
| 2009/0137911 A1 | 5/2009 | Sinderby et al. |
| 2009/0264833 A1* | 10/2009 | Boyle, Jr. ........... A61B 90/70 604/257 |
| 2010/0069725 A1 | 3/2010 | Al-Ali |
| 2010/0130947 A1 | 5/2010 | Daly |
| 2011/0071415 A1 | 3/2011 | Karwoski et al. |
| 2011/0152836 A1 | 6/2011 | Riopelle et al. |
| 2012/0172683 A1 | 7/2012 | Munoz-Bonet |
| 2012/0179009 A1 | 7/2012 | Gavriely |
| 2012/0289838 A1 | 11/2012 | Varga et al. |
| 2012/0302845 A1 | 11/2012 | Lynn |
| 2013/0053723 A1 | 2/2013 | Leveque et al. |
| 2013/0104884 A1 | 5/2013 | Vazales et al. |
| 2013/0110057 A1 | 5/2013 | Croteau et al. |
| 2013/0150701 A1 | 6/2013 | Budar et al. |
| 2013/0263855 A1 | 10/2013 | Tivig et al. |
| 2013/0323120 A1* | 12/2013 | Ma ............ A61L 2/24 422/24 |
| 2014/0000606 A1 | 1/2014 | Doyle et al. |
| 2014/0012096 A1 | 1/2014 | Nomura et al. |
| 2015/0031968 A1 | 1/2015 | Miserlis et al. |
| 2017/0368241 A1 | 12/2017 | Aho et al. |

OTHER PUBLICATIONS

International Preliminary Report on Patentability for PCT/US2015/064776, dated Jun. 13, 2017, 8 pages.

International Search Report and Written Opinion for PCT/US2015/064776, dated Mar. 11, 2016, 15 pages.

Pizano et al., "When should a chest radiograph be obtained after chest tube removal in mechanically ventilated patients? A prospective study," *J Trauma.*, 53(6):1073-1077, Dec. 2002.

Raffin et al., [Assessment of end-tidal CO2 in the pleural chest tube during lung volume reduction surgery], *Ann Fr Anesth Reanim.*, 22(5):484-486, May 2003, [Article in French] English abstract.

Anegg et al., "AIRFIX: the first digital postoperative chest tube airflowmetry—a novel method to quantify air leakage after lung resection," *Eur J Cardiothoracic Surg.*, 29(6):867-872, Jun. 1, 2006.

Brunelli et al., "Evaluation of a new chest tube removal protocol using digital air leak monitoring after lobectomy: a prospective randomised trial," *Eur J Cardiothoracic Surg.*, 37(1):56-60, Jan. 1, 2010.

\* cited by examiner

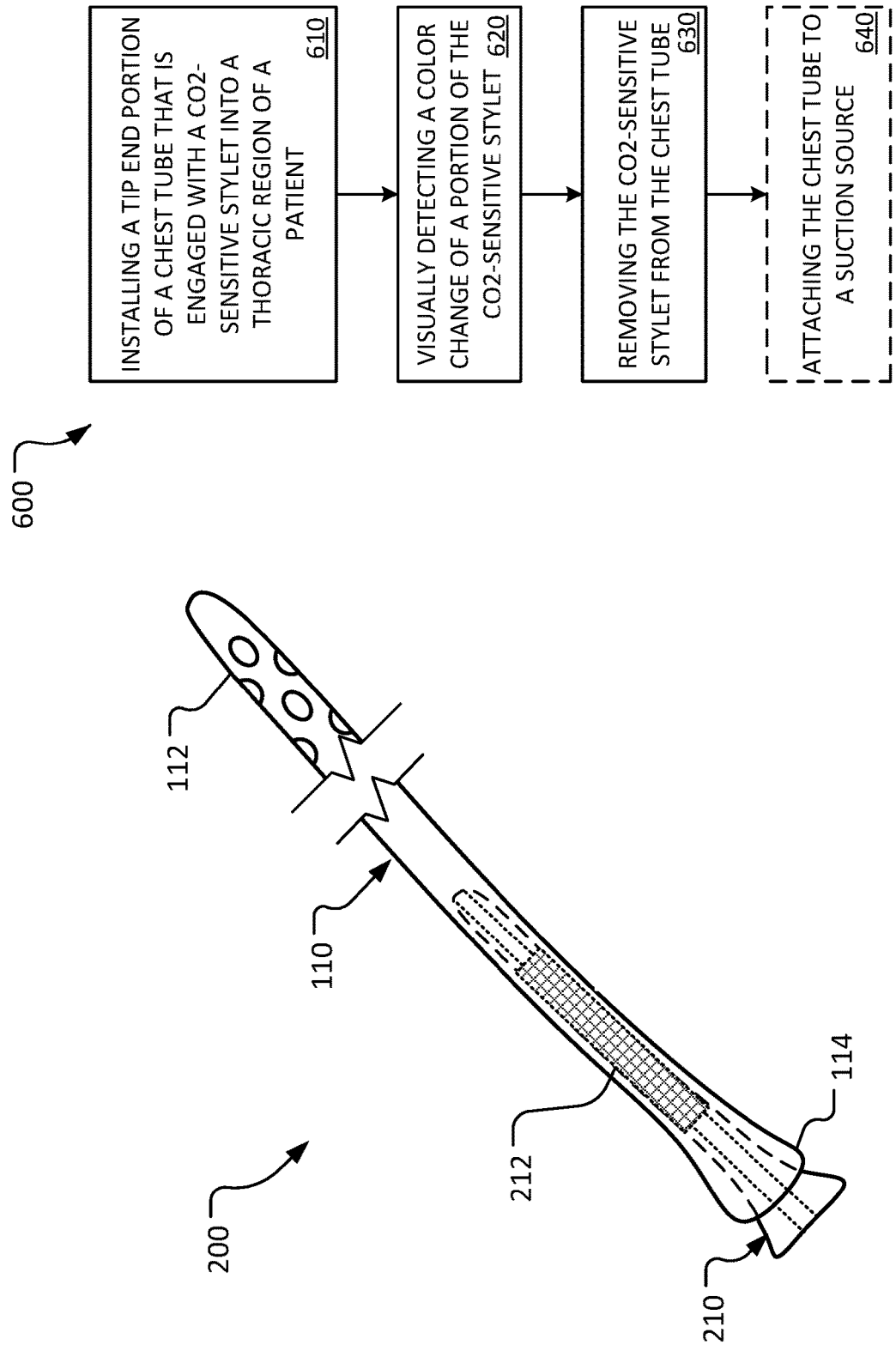

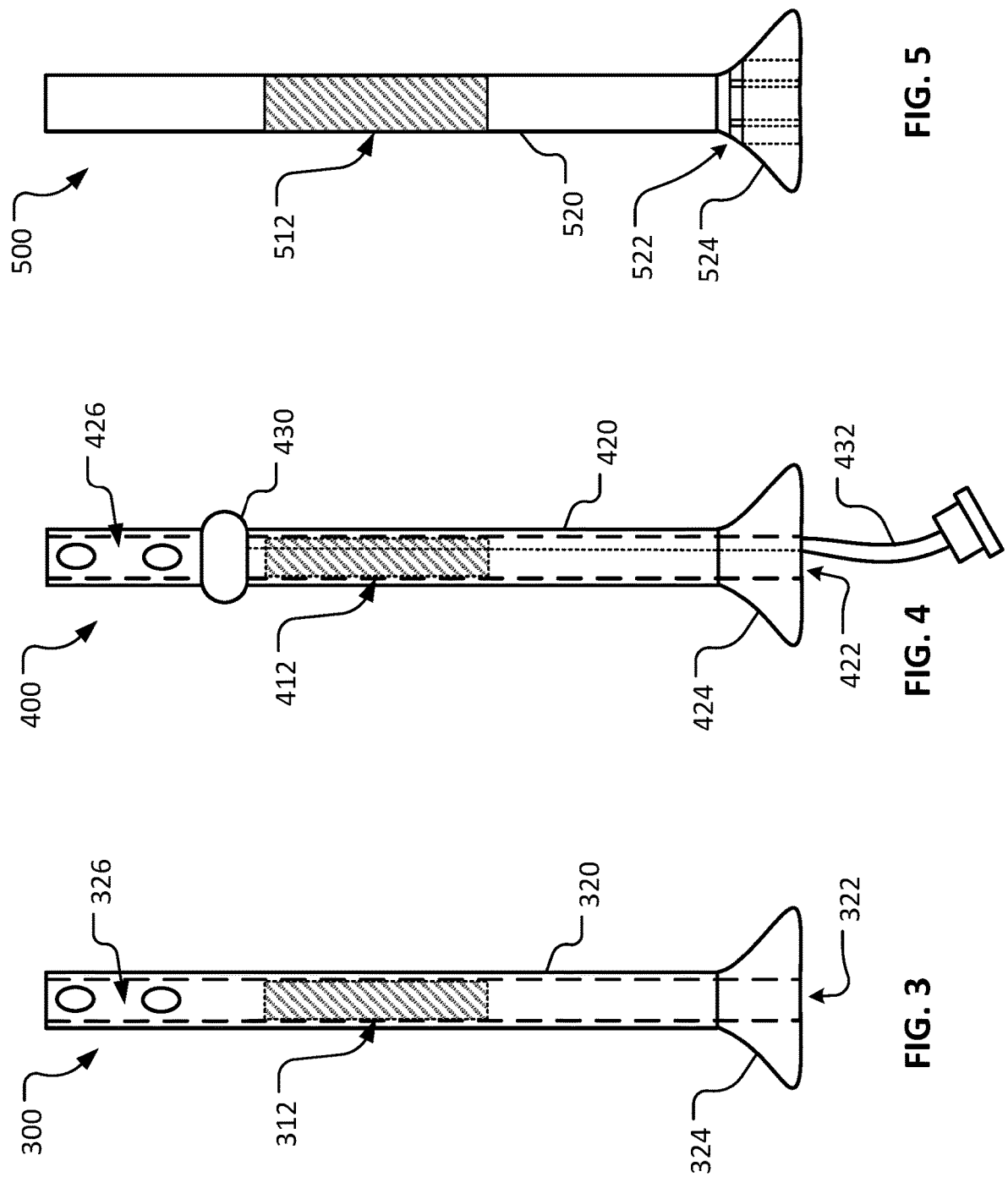

CO2-SENSING CHEST TUBE AND NEEDLE THORACOSTOMY DEVICES

CROSS REFERENCE TO RELATED APPLICATIONS

This application is a National Stage application under 35 U.S.C. § 371 of International Application No. PCT/US2015/064776, having an International Filing Date of Dec. 9, 2015, which claims the benefit of U.S. Provisional Application No. 62/089,909, filed Dec. 10, 2014. The disclosure of the prior application is considered part of and is incorporated by reference in the disclosure of this application.

STATEMENT AS TO FEDERALLY SPONSORED RESEARCH

This invention was made with government support under HL105355 awarded by the National Institutes of Health. The government has certain rights in the invention.

BACKGROUND

1. Technical Field

This document relates to systems and methods that can improve the efficacy of chest tube and needle thoracostomy. For example, this document relates to devices and methods for confirming the proper placement of a chest tube or needle within the pleural space to relieve a pneumothorax or tension pneumothorax.

2. Background Information

The lungs are paired organs that lie in the thoracic cavity. A gas transfer takes place in the lungs, with oxygen from inhaled air being transported into the blood, and carbon dioxide ($CO_2$) being removed from the blood. The $CO_2$ is then exhaled from the lungs.

Surrounding the lungs is a very thin space called the pleural space. The pleural space is usually very thin, and filled with a small amount of fluid. If air enters the pleural space, the lung will tend to collapse. This buildup of air in the pleural space puts pressure on the lung, so it cannot expand as much as it normally does from taking a breath. Progressive build-up of pressure in the pleural space pushes the mediastinum to the opposite hemithorax, and obstructs venous return to the heart. This leads to circulatory instability and may result in traumatic arrest. Such entrance of air into the pleural space is called a pneumothorax.

Air can enter the pleural space in various ways. If the chest wall is penetrated, which may occur as a result of an injury, air can enter the pleural space from the outside. More commonly, air can also enter from the inside, from the lung itself for example, if the lung is torn or ruptured. Another cause of pneumothorax is a pulmonary bleb. This is a weakness and out-pouching of the lung tissue, which can rupture.

Needle thoracsotomy for tension pneumothorax decompression is a potentially lifesaving emergency procedure. It is typically performed by emergency response crews, emergency medicine physicians, trauma surgeons, and critical care providers. Despite being theoretically lifesaving, the current body of evidence suggests there are major flaws with the procedure that result in high failure rates (e.g., up to 50%). The failure risk is largely due to the equipment used (e.g., a large bore needle) that may unreliably reach the chest cavity, and obstructs easily.

Thoracostomy (chest tubes) tubes are long, semi-stiff, clear plastic tubes that are inserted between the ribs into the chest so that they can drain collections of liquids or air from the pleural space. If the lung has been compressed because of this collection, the lung can then re-expand.

SUMMARY

This document provides systems and methods that can improve the efficacy of tube and needle thoracostomy. For example, this document provides devices and methods for confirming the proper placement of a chest tube or needle within the pleural space to relieve a pneumothorax or tension pneumothorax.

In one implementation, a chest tube thoracostomy system includes: a chest tube comprising a flexible tube defining a chest tube lumen, the flexible tube having a tip end portion and a connector end portion; and a $CO_2$-sensing stylet that is releasably coupleable with the chest tube such that at least a portion of the $CO_2$-sensing stylet is engaged within the chest tube lumen, the $CO_2$-sensing stylet comprising a $CO_2$-sensitive portion that is configured to change color in response to varying levels of $CO_2$ gas.

Such a chest tube thoracostomy system may optionally include one or more of the following features. The $CO_2$-sensing stylet may include a shaft that defines a longitudinal stylet lumen, and the $CO_2$-sensitive portion may be disposed on a wall of the stylet lumen. The chest tube thoracostomy system may further comprise an inflatable member disposed on the shaft, wherein the inflatable member can seal against the chest tube lumen when the inflatable member is in an expanded configuration. The shaft may define one or more fenestrations that are in fluid communication with the stylet lumen. The $CO_2$-sensing stylet may include a shaft, and the $CO_2$-sensitive portion may be disposed on an exterior wall of the shaft.

In another implementation, a method for installing a chest tube in a patient includes: installing a tip end portion of a chest tube that is engaged with a $CO_2$-sensing stylet into a thoracic region of the patient; visually detecting a color change to the $CO_2$-sensitive portion of the $CO_2$-sensing stylet; and removing the $CO_2$-sensing stylet from the chest tube while at least the tip end portion of the chest tube remains in the thoracic region of the patient. The chest tube comprises a flexible tube defining a chest tube lumen. The flexible tube has a tip end portion and a connector end portion. The $CO_2$-sensing stylet comprises a $CO_2$-sensitive portion that is configured to change color in response to varying levels of $CO_2$ gas. The $CO_2$-sensing stylet being releasably coupleable with the chest tube such that at least a portion of the $CO_2$-sensing stylet is engaged within the chest tube lumen.

Such a method for installing a chest tube in a patient may optionally include one or more of the following features. The method may further comprise attaching the installed chest tube to a suction source.

In another implementation, a $CO_2$-sensing stylet is provided that is configured to be releasably coupleable with a chest tube such that at least a portion of the $CO_2$-sensing stylet is engaged within a chest tube lumen of the chest tube. The $CO_2$-sensing stylet comprises a $CO_2$-sensitive portion that is configured to change color in response to varying levels of $CO_2$ gas.

Such a CO$_2$-sensing stylet may optionally include one or more of the following features. The CO$_2$-sensing stylet may include a shaft that defines a longitudinal stylet lumen, and the CO$_2$-sensitive portion may be disposed on a wall of the stylet lumen. The CO$_2$-sensing stylet may further comprise an inflatable member disposed on the shaft, wherein the inflatable member is configured to seal against the chest tube lumen when the inflatable member is in an expanded configuration. The shaft may define one or more fenestrations that are in fluid communication with the stylet lumen. The shaft may define one or more fenestrations that are in fluid communication with the stylet lumen. The CO$_2$-sensing stylet may include a shaft, and the CO$_2$-sensitive portion may be disposed on an exterior wall of the shaft. The CO$_2$-sensing stylet may further comprise an air-tight package that the CO$_2$-sensing stylet can be contained within.

In another implementation, a CO$_2$-sensing needle thoracostomy device includes a catheter shaft defining a longitudinal lumen and one or more fenestrations in fluid communication with the lumen. A sharp distal tip extends from the catheter shaft, and a CO$_2$-sensitive portion that is configured to change color in response to varying levels of CO$_2$ gas is disposed at an end of the catheter shaft that is opposite from the sharp distal tip.

Such a CO$_2$-sensing needle thoracostomy device may optionally include one or more of the following features. The CO$_2$-sensitive portion may be disposed on a wall of the lumen. The CO$_2$-sensing needle thoracostomy device may further comprise an air-tight package that the CO$_2$-sensing needle thoracostomy device can be contained within.

In another implementation, a CO$_2$-sensing needle thoracostomy device includes a catheter shaft defining an open distal end, an open proximal end, and a longitudinal lumen extending between the open distal end and the open proximal end. The CO$_2$-sensing needle thoracostomy device also includes a CO$_2$-sensitive portion disposed proximate the open proximal end that is configured to change color in response to varying levels of CO$_2$ gas. The CO$_2$-sensing needle thoracostomy device also includes an introducer needle slidably disposed within the lumen, wherein the introducer needle includes a sharp distal tip configured for puncturing tissue.

Such a CO$_2$-sensing needle thoracostomy device may optionally include one or more of the following features. The catheter shaft may further define one or more fenestrations proximate to the open distal end. The CO$_2$-sensitive portion may be disposed on a wall of the lumen. The CO$_2$-sensing needle thoracostomy device may further comprise an air-tight package that the CO$_2$-sensing needle thoracostomy device can be contained within. The introducer needle may provide an air-tight seal of the CO$_2$-sensitive portion while the introducer needle is disposed within the lumen.

Particular embodiments of the subject matter described in this document can be implemented to realize one or more of the following advantages. First, in some embodiments the devices and methods provided herein can be used to confirm whether a chest tube or needle thoracostomy device is properly placed within a patient's pleural space. In some circumstances, such devices and methods can provide more a definitive confirmation of proper chest tube or needle thoracostomy device placement than current methods. For example, chest radiographs are sometimes currently used in attempt to confirm the proper placement of chest tubes. However, such radiographical images typically provide only two-dimensional visualization. Therefore, a chest radiograph may not provide a definitive confirmation of the three-dimensional location of the chest tube within the patient's pleural space.

Second, in some embodiments the devices and methods provided herein can be used to confirm proper chest tube or needle thoracostomy device placement with greater objectivity than some current techniques. For example, in another current technique used in attempt to confirm proper chest tube placement, a visual inspection of the passage of gas bubbles through a water-seal chest drainage unit is performed. However, such visual inspection is inherently subjective and prone to human error. In contrast, in some embodiments the devices and methods provided herein allow for objective detection and verification of the proper placement of chest tubes or needle thoracostomy device by monitoring CO$_2$ extracted from the pleural space.

Third, in some embodiments the devices and methods provided herein can assist with a determination of whether an air leak is an internal or an external air leak. Such a determination can be made at least in part in view of the level of CO$_2$ from the pleural space that is detected by the CO$_2$-sensing stylets or needle thoracostomy devices provided herein.

Other advantages will be discernable in view of the specification and figures described below.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 2 is a plan view of an example chest tube that is engaged with an example CO$_2$-sensing stylet in accordance with some embodiments.

FIG. 3 is a plan view of an example CO$_2$-sensing stylet in accordance with some embodiments.

FIG. 4 is a plan view of another example CO$_2$-sensing stylet in accordance with some embodiments.

FIG. 5 is a plan view of another example CO$_2$-sensing stylet in accordance with some embodiments.

FIG. 6 is a flowchart of a method for confirming proper placement of a chest tube in a pleural space in accordance with some embodiments provided herein.

Like reference numbers represent corresponding parts throughout.

DETAILED DESCRIPTION

This document provides systems and methods that can improve the efficacy of tube and needle thoracostomy. For example, this document provides devices and methods for confirming the proper placement of a chest tube or a needle within the pleural space to relieve a pneumothorax or tension pneumothoax.

Pneumothorax (air in the pleural space) can be life-threatening. The immediate treatments for pneumothorax are tube or needle thoracostomy, or the insertion of a chest tube or a needle device to relieve pressure from the pleural space. A long, flexible, hollow, narrow tube (chest tube) or a shorter needle is inserted through the ribs into the pleural space. The chest tube is attached to a suction device. This allows the air to be evacuated from the pleural space, and allows the lung to re-expand. Chest tubes are generally inserted using local anesthesia. The chest tube is left in place until the lung leak seals on its own, which usually occurs within two to five days.

Some pneumothorax conditions can be characterized by the presence of $CO_2$ in the air within the pleural space. For example, when a lung is punctured, some of the air that is exhaled from the lung will escape into the pleural space. In that circumstance, $CO_2$ from the exhaled air will be present within the pleural space. When a chest tube or needle thoracostomy system is used in that scenario to treat pneumothorax, $CO_2$ will be present in the gas that is removed from the pleural space by the chest tube or needle device. Therefore, the presence of $CO_2$ in the gas removed by the chest tube or needle device can be indicative of a chest tube or needle device that is properly placed so as to remove gas from the pleural space.

Figure 1:
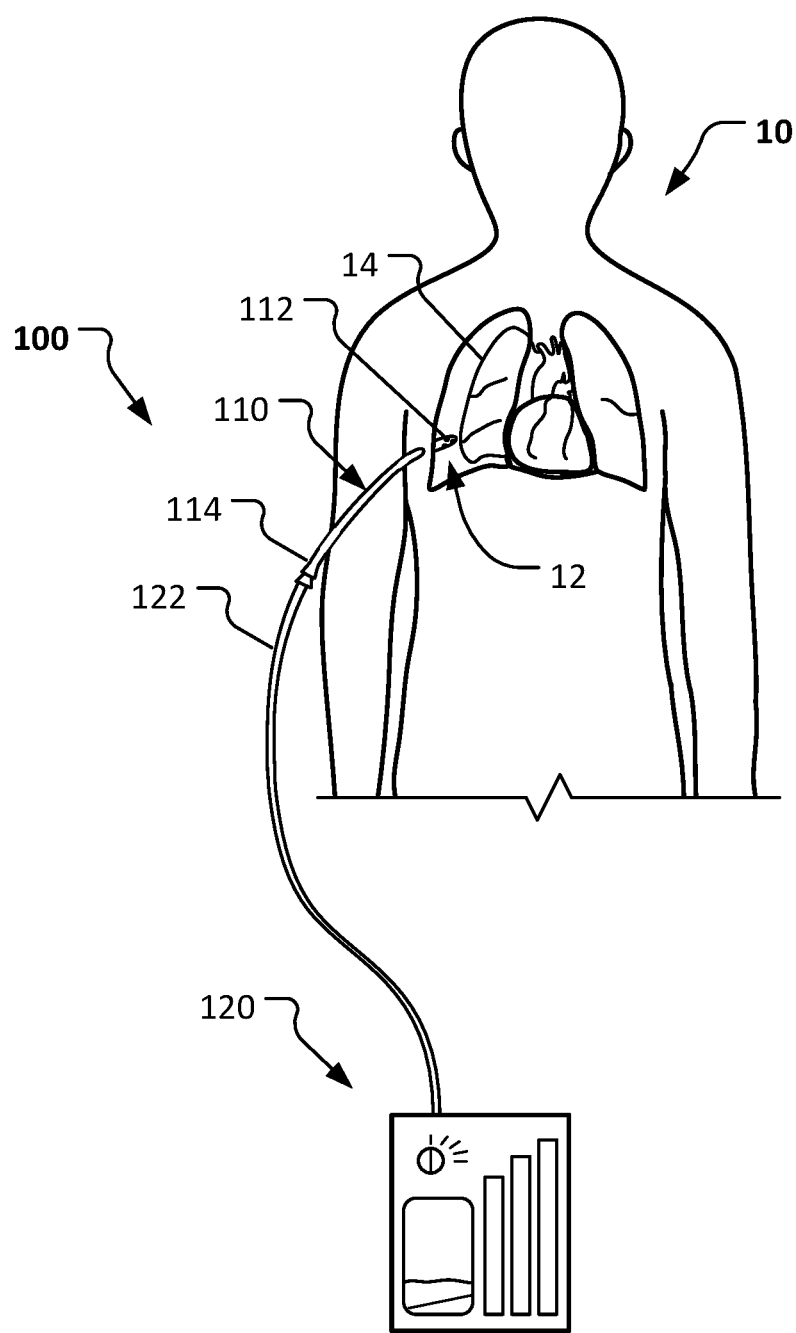
FIG. 1 is a schematic diagram of patient undergoing a chest tube thoracostomy in accordance with some embodiments provided herein.

Referring to FIG. 1, a patient 10 is undergoing a tube thoracostomy procedure using a tube thoracostomy system 100. Tube thoracostomy system 100 includes, in general, a chest tube 110 and a suction source such as a water-seal chest drainage unit (CDU) 120.

Chest tube 110 is inserted into patient 10 and positioned so that a tip end portion 112 of chest tube 110 is in a pleural space 12 near a partially collapsed lung 14 of patient 10. Tip end portion 112 includes one or more fenestrations so that the lumen of chest tube 110 is in fluid communication with pleural space 12. A connection end portion 114 of chest tube 110 is connected to flexible tube 122 of CDU 120. CDU 120 thereby provides a source of suction that is conveyed through chest tube 110 to assist with evacuation of air from pleural space 12.

As described further herein, in some embodiments chest tube 110 initially includes a stylet component that is configured to sense the presence of $CO_2$ in chest tube 110. The presence of $CO_2$ can thereby be observed by a clinician to confirm whether there is $CO_2$ present in the gas that is being evacuated from pleural space 12 of patient 10 via chest tube 110. In some circumstances, the clinician can thereby confirm whether chest tube 110 is properly positioned within pleural space 12.

Referring to FIG. 2, a chest tube system 200 includes chest tube 110 and a $CO_2$-sensing stylet 210. $CO_2$-sensing stylet 210 is slidably coupled within chest tube 110 at connection end portion 114. The depicted configuration of chest tube system 200 is the configuration that would be used when inserting chest tube 110 into the pleural space of a patient.

When chest tube system 200 is inserted into the pleural space of a patient, if there is $CO_2$ in the pleural space, the $CO_2$ will tend to have a positive pressure in relation to atmospheric pressure. Therefore, the $CO_2$ in the pleural space will tend to enter tip end 112 of chest tube 110 and flow towards $CO_2$-sensing stylet 210.

As the $CO_2$ passes along $CO_2$-sensing stylet 210, some of the $CO_2$ will come into contact with a $CO_2$-sensitive portion 212 of $CO_2$-sensing stylet 210. $CO_2$-sensitive portion 212 (as with the other $CO_2$-sensitive portions described herein) can utilize a number of different $CO_2$ detection apparatuses and modalities. For example, in some embodiments a colorimetric sensing device is used. Moreover, all other suitable $CO_2$ detection devices and modalities can also be used, such as, but not limited to, near-infrared spectroscopy (NIRS), chemical gas sensors, and the like. While colorimetric $CO_2$ detection is described in the context of the devices provided herein, it should be understood that the devices are not limited to colorimetric $CO_2$ detection, and all other suitable $CO_2$ detection devices and modalities can additionally or alternatively be used.

When $CO_2$ comes into contact with colorimetric $CO_2$-sensitive portion 212, a color change that is visually detectable by the clinician will occur to colorimetric $CO_2$-sensitive portion 212. Hence, by visualizing a color change of colorimetric $CO_2$-sensitive portion 212, a clinician will be able to confirm that chest tube 110 is properly positioned within the pleural space. For example, in some embodiments colorimetric $CO_2$-sensitive portion 212 may appear blue when essentially no $CO_2$ is present, green when a small amount of $CO_2$ is present, and yellow when an appreciable amount of $CO_2$ is present. In some embodiments, other indicators may be used. The color change to colorimetric $CO_2$-sensitive portion 212 will be visible through the essentially transparent or translucent wall of chest tube 110.

In some embodiments, without limitation, colorimetric $CO_2$-sensitive portion 212 comprises a borosilicate substrate with a $CO_2$-responsive indicator solution thereon. Such a construct can provide for colorimetric $CO_2$ detection. In some embodiments, other types of constructs can be used for colorimetric $CO_2$-sensitive portion 212.

In some embodiments, a pull-tab barrier is included that prevents air contact with $CO_2$-sensitive portion 212 prior to use. The barrier can be removed just prior to insertion of $CO_2$-sensing stylet 210 within a chest tube 110. In some embodiments, chest tube 110 with $CO_2$-sensing stylet 210 pre-installed therein may be packaged as an assembly within a unit package (e.g., a pouch, tray, wrap, and the like). The unit package may be sealed to prevent air contact with $CO_2$-sensitive portion 212 prior to use.

After proper placement of chest tube system 200 in the pleural space, as confirmed by a color change of $CO_2$-sensitive portion 212, $CO_2$-sensing stylet 210 can be slidably removed from chest tube 110. Then chest tube 110 can be connected with a suction source such as water-seal CDU 120 (refer to FIG. 1). $CO_2$-sensing stylet 210 can then be disposed of.

Referring to FIG. 3, an example $CO_2$-sensing stylet 300 includes a $CO_2$-sensitive portion 312 that is attached to a stylet shaft 320. $CO_2$-sensing stylet 300 is configured for releasable engagement with a chest tube, such as depicted in FIG. 2, for example.

In some embodiments, stylet shaft 320 includes a longitudinal lumen 322. In some embodiments, longitudinal lumen 322 extends from an optionally flanged end 324 to an optionally fenestrated tip end portion 326. Lumen 322 can provide a passageway for gases from the pleural space to escape (vent) from the interior of the chest tube when $CO_2$-sensing stylet 300 is engaged with the chest tube and the chest tube is inserted into the pleural space.

In some embodiments, $CO_2$-sensitive portion 312 is a material that is laminated to stylet shaft 320. In the depicted embodiment, $CO_2$-sensitive portion 312 is laminated to the wall of lumen 322. Therefore, as gases from the pleural space pass through lumen 322, the gases will come into contact with $CO_2$-sensitive portion 312. If $CO_2$ is a constituent of the gases, a color change of $CO_2$-sensitive portion 312 may result. The color change of $CO_2$-sensitive portion 312 can be visually detected by a clinician, and proper placement of the chest tube can thereby be verified. In some implementations, suction may be applied to lumen 322 at optionally flanged end 324 to encourage the gases from the pleural space to pass through lumen 322, and thereby contact $CO_2$-sensitive portion 312. After the visual verification of the color change of $CO_2$-sensitive portion 312, $CO_2$-sensing stylet 300 can be removed from the chest tube and discarded.

Referring to FIG. 4, an example $CO_2$-sensing stylet 400 includes a $CO_2$-sensitive portion 412 that is attached to a stylet shaft 420. $CO_2$-sensing stylet 400 is configured for releasable engagement with a chest tube, such as depicted in FIG. 2, for example.

In some embodiments, stylet shaft 420 includes a longitudinal lumen 422. In some embodiments, longitudinal lumen 422 extends from an optionally flanged end 424 to an optionally fenestrated tip end portion 426. Lumen 422 can provide a passageway for gases from the pleural space to escape (vent) from the interior of the chest tube when $CO_2$-sensing stylet 400 is engaged with the chest tube and the chest tube is inserted into the pleural space.

In some embodiments, $CO_2$-sensing stylet 400 includes an inflatable sealing member 430. Inflatable sealing member 430 is in fluid communication with an inflation lumen 432. Injecting an inflation medium into inflatable sealing member 430 via inflation lumen 432 will cause inflatable sealing member 430 to enlarge. Conversely, venting or withdrawing inflation medium from inflatable sealing member 430 via inflation lumen 432 will cause inflatable sealing member 430 to collapse.

Inflatable sealing member 430 is configured to seal with the lumen of a chest tube (e.g., in the configuration shown in FIG. 2). One advantage provided by inflatable sealing member 430 is that, when inflated so as to seal with the lumen of a chest tube, virtually all gases passing through the chest tube will also pass through lumen 422. Therefore, virtually all gases passing through the chest tube will also come into contact with $CO_2$-sensitive portion 412.

In some embodiments, $CO_2$-sensitive portion 412 is a material that is laminated to stylet shaft 420. In the depicted embodiment, $CO_2$-sensitive portion 412 is laminated to the wall of lumen 422. Therefore, as gases from the pleural space pass through lumen 422, the gases will come into contact with $CO_2$-sensitive portion 412. If $CO_2$ is a constituent of the gases, a color change of $CO_2$-sensitive portion 412 may result. The color change of $CO_2$-sensitive portion 412 can be visually detected by a clinician, and proper placement of the chest tube can thereby be verified. In some implementations, suction may be applied to lumen 422 at optionally flanged end 424 to encourage the gases from the pleural space to pass through lumen 422, and thereby contact $CO_2$-sensitive portion 412. After the visual verification of the color change of $CO_2$-sensitive portion 412, $CO_2$-sensing stylet 400 can be removed from the chest tube and discarded.

Referring to FIG. 5, an example $CO_2$-sensing stylet 500 includes a $CO_2$-sensitive portion 512 that is attached to a stylet shaft 520. $CO_2$-sensing stylet 500 is configured for releasable engagement with a chest tube, such as depicted in FIG. 2, for example.

In some embodiments, stylet shaft 520 includes an optional gas passageway 522 at an optionally flanged end 524. The depicted embodiment does not include a longitudinal lumen as included in some other embodiments described herein. Gas passageway 522 can provide a passageway for gases from the pleural space to escape (vent) from the interior of the chest tube when $CO_2$-sensing stylet 500 is engaged with the chest tube and the chest tube is inserted into the pleural space. Alternately, gas passageway 522 can be omitted and gases can simply pass through spaces between $CO_2$-sensing stylet 500 and the chest tube.

In some embodiments, $CO_2$-sensitive portion 512 is a material that is laminated to stylet shaft 520. In the depicted embodiment, $CO_2$-sensitive portion 512 is laminated to the exterior wall of stylet shaft 520. Therefore, as gases from the pleural space along stylet shaft 520, the gases will come into contact with $CO_2$-sensitive portion 512. If $CO_2$ is a constituent of the gases, a color change of $CO_2$-sensitive portion 512 may result. The color change of $CO_2$-sensitive portion 512 can be visually detected by a clinician, and proper placement of the chest tube can thereby be verified. In some implementations, suction may be applied to gas passageway 522 at optionally flanged end 524 to encourage the gases from the pleural space to pass through gas passageway 522, and thereby contact $CO_2$-sensitive portion 512. After the visual verification of the color change of $CO_2$-sensitive portion 512, $CO_2$-sensing stylet 500 can be removed from the chest tube and discarded.

It should be understood that one or more features described in the context of a particular $CO_2$-sensing stylet embodiment can be combined with one or more features that are described in the context of one or more other $CO_2$-sensing stylet embodiments. Hence, the features of the $CO_2$-sensing stylets described herein can be mixed and matched to arrive at hybrid designs of any and all possible combinations and permutations, and such hybrid designs are within the scope of this disclosure.

Referring to FIG. 6, a method 600 for installing a chest tube in a patient includes the use of a $CO_2$-sensing stylet as provided herein. During installation of the chest tube, the $CO_2$-sensing stylet is engaged with the chest tube as depicted in FIG. 2.

At step 610, a clinician installs a tip end portion of a chest tube that is engaged with a $CO_2$-sensing stylet into a thoracic region of the patient. In doing so, the tip end portion may enter the pleural space that may contain $CO_2$. Detection of the $CO_2$ can be used as an indicator that the chest tube is properly positioned within the patient.

At step 620, the clinician can visually detect a color change to a portion of the $CO_2$-sensing stylet. The color change occurs to the $CO_2$-sensitive portion of the $CO_2$-sensing stylet, as described above. Such a color change indicates the presence of $CO_2$, which in turn indicates that the chest tube is properly positioned within the patient.

At step 630, the clinician can remove the $CO_2$-sensing stylet from the chest tube. In some embodiments, the clinician may thereafter discard the $CO_2$-sensing stylet.

At step 640, the clinician can optionally attach the installed chest tube to a suction source. Such a suction source may be used to provide therapeutic benefits, in conjunction with the chest tube, to the patient.

Figure 7:
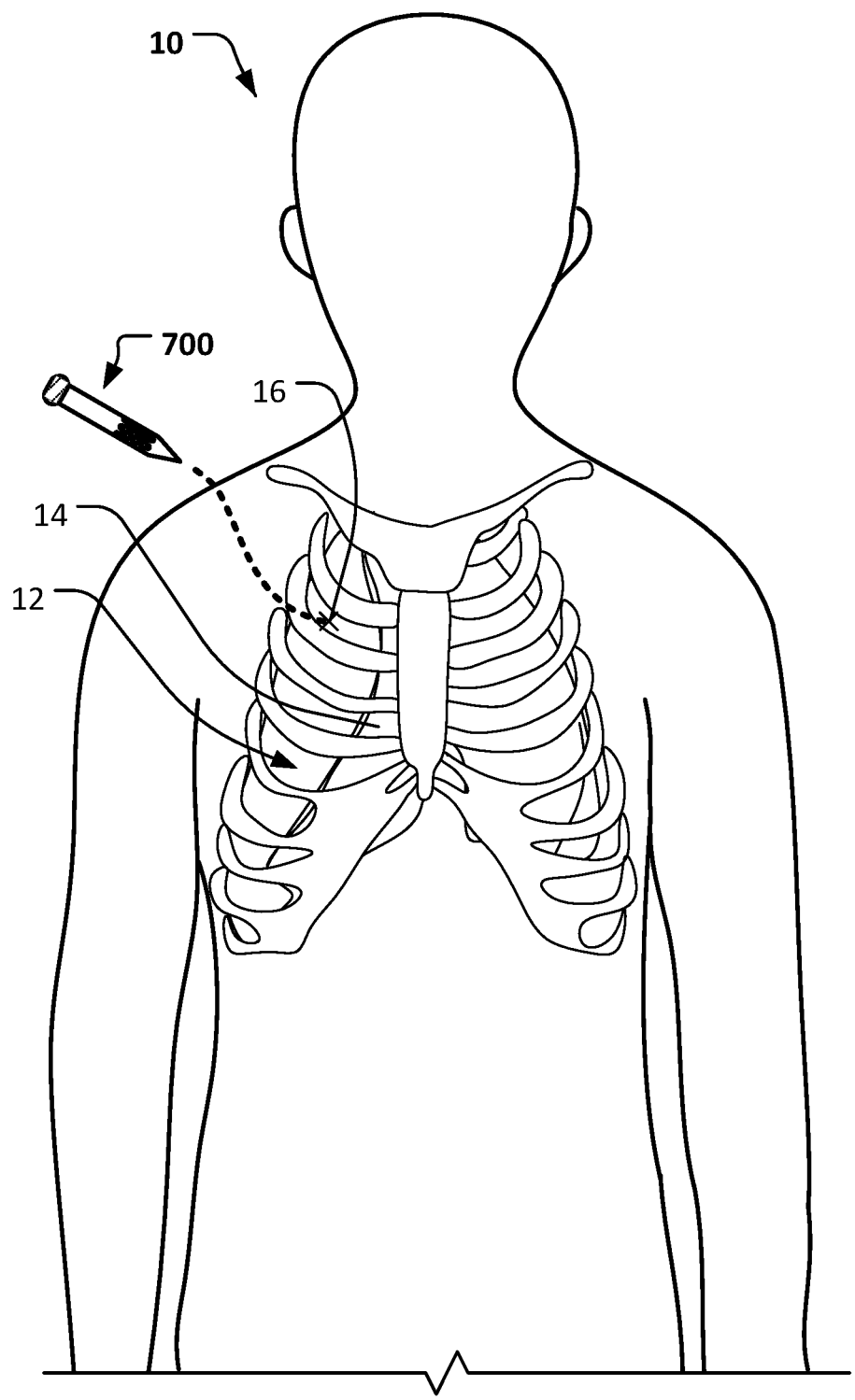
FIG. 7 is a schematic diagram of patient undergoing a needle thoracostomy in accordance with some embodiments.

Referring to FIG. 7, patient 10 is about to undergo a needle thoracostomy procedure using a needle thoracostomy device 700. When needle thoracostomy device 700 is properly inserted in patient 10, air from pleural space 12 near partially collapsed lung 14 will be vented external of patient 10. Typically, needle thoracostomy device 700 will be inserted into the second rib space 16 in the mid-clavicular line.

Figure 8:
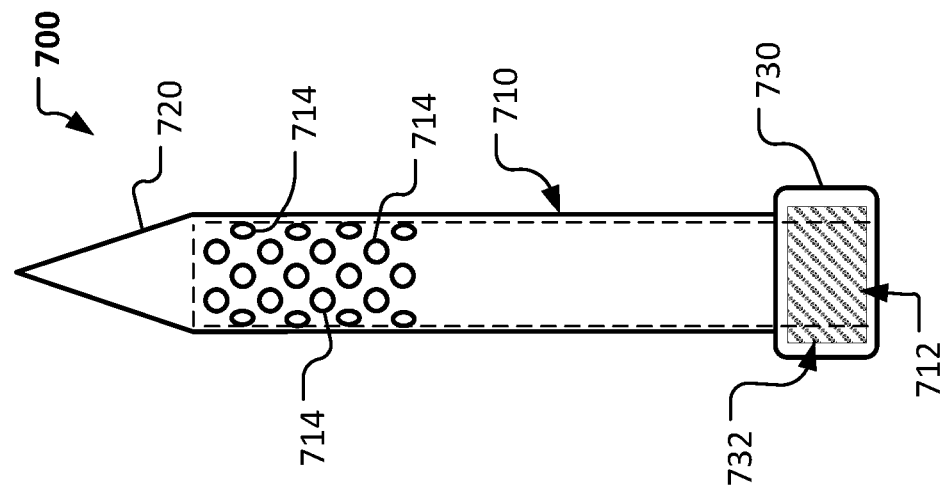
FIG. 8 is a plan view of an example CO$_2$-sensing needle thoracostomy device in accordance with some embodiments.

Referring also to FIG. 8, in some embodiments needle thoracostomy device 700 includes a catheter shaft 710 with a distal sharp end 720 and a proximal hub 730. Catheter shaft 710 defines a longitudinal lumen 712 and one or more fenestrations 714 that are in fluid communication with lumen 712. Hence, when needle thoracostomy device 700 is inserted into patient 10, pressurized air from pleural space 12 can pass through fenestrations 714 and into lumen 712. Pressurized air can then exit lumen 712 at proximal hub 730 such that pressure in pleural space 12 can be relieved external of patient 10.

Needle thoracostomy device 700 can be made of metals (e.g., stainless steels) or plastics, or a combination thereof.

Distal sharp end 720 is a needle-like tip configured for puncturing tissue and penetrating into the pleural space. Hence, needle thoracostomy device 700 can be pressed into patient 10 by a clinician or emergency personnel to perform a needle thoracostomy.

Proximal hub 730 includes a $CO_2$-sensitive portion 732. The presence of $CO_2$ can thereby be observed by a clinician to confirm whether there is $CO_2$ present in the gas that is being evacuated from pleural space 12 of patient 10 via needle thoracostomy device 700. In some circumstances, the clinician can thereby confirm whether needle thoracostomy device 700 is properly positioned within pleural space 12.

When needle thoracostomy device 700 is inserted into the pleural space 12 of patient 10, if there is $CO_2$ in the pleural space, the $CO_2$ will tend to have a positive pressure in relation to atmospheric pressure. Therefore, the $CO_2$ in the pleural space will tend to enter fenestrations 714 of needle thoracostomy device 700 and flow towards $CO_2$-sensing portion 732.

As the $CO_2$ passes through lumen 712, some of the $CO_2$ will come into contact with colorimetric $CO_2$-sensitive portion 732 of proximal hub 730. When $CO_2$ comes into contact with colorimetric $CO_2$-sensitive portion 732, a color change that is visually detectable by the clinician will occur to colorimetric $CO_2$-sensitive portion 732. Hence, by visualizing a color change of colorimetric $CO_2$-sensitive portion 732, a clinician will be able to confirm that needle thoracostomy device 700 is properly positioned within the pleural space 12. For example, in some embodiments colorimetric $CO_2$-sensitive portion 732 may appear blue when essentially no $CO_2$ is present, green when a small amount of $CO_2$ is present, and yellow when an appreciable amount of $CO_2$ is present. In some embodiments, other indicators may be used. The color change to colorimetric $CO_2$-sensitive portion 732 will be visible through the essentially transparent or translucent wall of proximal hub 730.

In some embodiments, without limitation, colorimetric $CO_2$-sensitive portion 732 comprises a borosilicate substrate with a $CO_2$-responsive indicator solution thereon. Such a construct can provide for colorimetric $CO_2$ detection. In some embodiments, other types of constructs can be used for colorimetric $CO_2$-sensitive portion 732.

In some embodiments, a pull-tab barrier is included that prevents air contact with $CO_2$-sensitive portion 732 prior to use. The barrier can be removed just prior to insertion of $CO_2$-sensing needle thoracostomy device 700. In some embodiments, $CO_2$-sensing needle thoracostomy device 700 may be packaged within a unit package (e.g., a pouch, tray, wrap, and the like). The unit package may be sealed to prevent air contact with $CO_2$-sensitive portion 732 prior to use.

After proper placement of $CO_2$-sensing needle thoracostomy device 700 in the pleural space, as confirmed by a color change of $CO_2$-sensitive portion 732, $CO_2$-sensing needle thoracostomy device 700 facilitates effective tension pneumothorax decompression.

Figure 9:
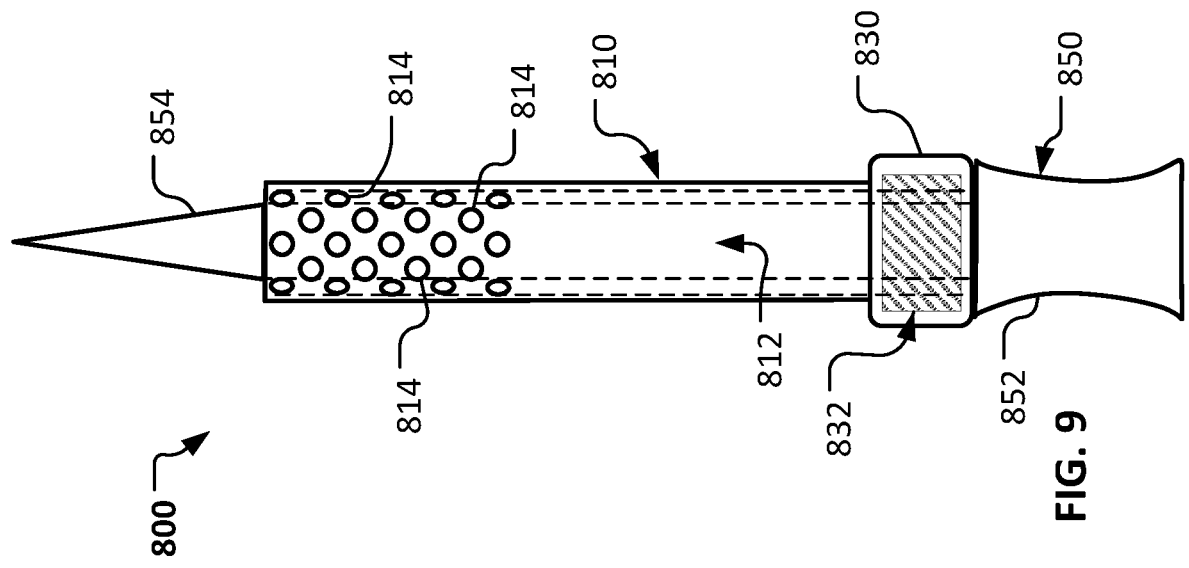
FIG. 9 is a plan view of another example $CO_2$-sensing needle thoracostomy device in accordance with some embodiments.

Referring to also FIG. 9, in some embodiments another example needle thoracostomy device 800 includes a catheter shaft 810 and an introducer needle 850 slidably disposed within a lumen 812 defined by catheter shaft 810. Catheter shaft includes a proximal hub 830 and optionally defines one or more fenestrations 814 that are in fluid communication with lumen 812. Hence, when needle thoracostomy device 800 is inserted into patient 10, introducer needle 850 can be slidably removed from catheter shaft 810, and pressurized air from pleural space 12 can pass through fenestrations 814 and into lumen 812. Pressurized air can then exit lumen 812 at proximal hub 830 such that pressure in pleural space 12 can be relieved external of patient 10.

Needle thoracostomy device 800 can be made of metals (e.g., stainless steels) or plastics, or a combination thereof.

Introducer needle 850 includes a distal sharp end 854 and a proximal hub 852. Distal sharp end 854 is a needle-like tip configured for puncturing tissue and penetrating into the pleural space. Hence, needle thoracostomy device 800 can be pressed into patient 10 by a clinician or emergency personnel to perform a needle thoracostomy. When needle thoracostomy device 800 has been inserted into patient 10, introducer needle 850 can then be removed by pulling proximally on proximal hub 852.

Proximal hub 830 includes a $CO_2$-sensitive portion 832. The presence of $CO_2$ can thereby be observed by a clinician to confirm whether there is $CO_2$ present in the gas that is being evacuated from pleural space 12 of patient 10 via needle thoracostomy device 800. In some circumstances, the clinician can thereby confirm whether needle thoracostomy device 800 is properly positioned within pleural space 12.

When needle thoracostomy device 800 is inserted into the pleural space 12 of patient 10, if there is $CO_2$ in the pleural space, the $CO_2$ will tend to have a positive pressure in relation to atmospheric pressure. Therefore, the $CO_2$ in the pleural space will tend to enter fenestrations 814 of needle thoracostomy device 800 and flow towards $CO_2$-sensing portion 832.

As the $CO_2$ passes through lumen 812, some of the $CO_2$ will come into contact with colorimetric $CO_2$-sensitive portion 832 of proximal hub 830. When $CO_2$ comes into contact with colorimetric $CO_2$-sensitive portion 832, a color change that is visually detectable by the clinician will occur to colorimetric $CO_2$-sensitive portion 832. Hence, by visualizing a color change of colorimetric $CO_2$-sensitive portion 832, a clinician will be able to confirm that needle thoracostomy device 800 is properly positioned within the pleural space 12. For example, in some embodiments colorimetric $CO_2$-sensitive portion 832 may appear blue when essentially no $CO_2$ is present, green when a small amount of $CO_2$ is present, and yellow when an appreciable amount of $CO_2$ is present. In some embodiments, other indicators may be used. The color change to colorimetric $CO_2$-sensitive portion 832 will be visible through the essentially transparent or translucent wall of proximal hub 830.

In some embodiments, without limitation, colorimetric $CO_2$-sensitive portion 832 comprises a borosilicate substrate with a $CO_2$-responsive indicator solution thereon. Such a construct can provide for colorimetric $CO_2$ detection. In some embodiments, other types of constructs can be used for colorimetric $CO_2$-sensitive portion 832.

In some embodiments, a pull-tab barrier is included that prevents air contact with $CO_2$-sensitive portion 832 prior to use. The barrier can be removed just prior to insertion of $CO_2$-sensing needle thoracostomy device 800. In some embodiments, $CO_2$-sensing needle thoracostomy device 800 may be packaged within a unit package (e.g., a pouch, tray, wrap, and the like). The unit package may be sealed to prevent air contact with $CO_2$-sensitive portion 832 prior to use. In some embodiments, introducer needle 850 may provide an air-tight seal such that ambient air does not contact $CO_2$-sensitive portion 832 prior to use (until introducer needle 850 is removed from catheter shaft 810).

After proper placement of $CO_2$-sensing needle thoracostomy device 800 in the pleural space, as confirmed by a color change of $CO_2$-sensitive portion 832, $CO_2$-sensing needle thoracostomy device 800 facilitates effective tension pneumothorax decompression. While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A chest tube thoracostomy system comprising:
a chest tube comprising a flexible tube defining a chest tube lumen, the flexible tube having a tip end portion and a connector end portion; and
a $CO_2$-sensing stylet that is releasably coupleable with the chest tube such that at least a portion of the $CO_2$-sensing stylet is engaged within the chest tube lumen, the $CO_2$-sensing stylet comprising:
a shaft that defines a longitudinal stylet lumen;
a $CO_2$-sensitive portion that is configured to change color in response to varying levels of $CO_2$ gas, wherein the $CO_2$-sensitive portion is disposed on a wall of the stylet lumen; and
an inflatable member disposed on the shaft, wherein the inflatable member can seal against the chest tube lumen when the inflatable member is in an expanded configuration.

2. The chest tube thoracostomy system of claim 1, wherein the shaft defines one or more fenestrations that are in fluid communication with the stylet lumen.

3. A $CO_2$-sensing stylet, wherein the $CO_2$-sensing stylet is configured to be releasably coupleable with a chest tube such that at least a portion of the $CO_2$-sensing stylet is engaged within a chest tube lumen of the chest tube, and wherein the $CO_2$-sensing stylet comprises:
a shaft that defines a longitudinal stylet lumen;
a $CO_2$-sensitive portion that is configured to change color in response to varying levels of $CO_2$ gas, wherein the $CO_2$-sensitive portion is disposed on a wall of the stylet lumen; and
an inflatable member disposed on the shaft, wherein the inflatable member is configured to seal against the chest tube lumen when the inflatable member is in an expanded configuration.

4. The $CO_2$-sensing stylet of claim 3, wherein the shaft defines one or more fenestrations that are in fluid communication with the stylet lumen.

5. The chest tube thoracostomy system of claim 1, further comprising an inflation lumen in fluid communication with the inflatable member.

6. The chest tube thoracostomy system of claim 1, wherein the $CO_2$-sensing stylet includes a flanged end.

7. The chest tube thoracostomy system of claim 1, wherein a tip end portion of the shaft defines one or more fenestrations that are in fluid communication with the stylet lumen.

8. The chest tube thoracostomy system of claim 1, wherein the $CO_2$-sensing stylet is slidably coupleable within the chest tube lumen.

9. The $CO_2$-sensing stylet of claim 3, further comprising an inflation lumen in fluid communication with the inflatable member.

10. The $CO_2$-sensing stylet of claim 3, wherein the $CO_2$-sensing stylet includes a flanged end.

11. The $CO_2$-sensing stylet of claim 3, wherein a tip end portion of the shaft defines one or more fenestrations that are in fluid communication with the stylet lumen.

* * * * *